United States Patent [19]

Burton et al.

[11] 4,267,829
[45] May 19, 1981

[54] PENILE PROSTHESIS

[75] Inventors: John H. Burton, Minnetonka; Michael A. Mikulich, St. Paul, both of Minn.

[73] Assignee: American Medical Systems, Inc., Minneapolis, Minn.

[21] Appl. No.: 108,124

[22] Filed: Dec. 28, 1979

Related U.S. Application Data

[63] Continuation-in-part of Ser. No. 28,979, Apr. 11, 1979, Pat. No. 4,224,934.

[51] Int. Cl.³ .............................................. A61F 5/00
[52] U.S. Cl. .................................................... 128/79
[58] Field of Search .......................................... 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 3,987,789 | 10/1976 | Timm et al. | 128/79 |
| 4,009,711 | 3/1977 | Uson | 128/79 |

Primary Examiner—John D. Yasko
Attorney, Agent, or Firm—Williamson, Bains, Moore & Hansen

[57] ABSTRACT

This implantable penile prosthesis may be surgically implanted in human males to cure erectile impotence. The prosthesis includes a pair of rigid portions joined by a hollow tubular section, all of which are implanted inside and along the length of a penis. The tubular section is connected to a pump means which controls erection of the penis by controlling the supply of fluid pressure to the tubular section. The tubular section includes a chamber means which undergoes only a small change in volume and therefore requires minimal fluid displacement as the prosthesis goes between a nonerect and an erect condition.

14 Claims, 6 Drawing Figures

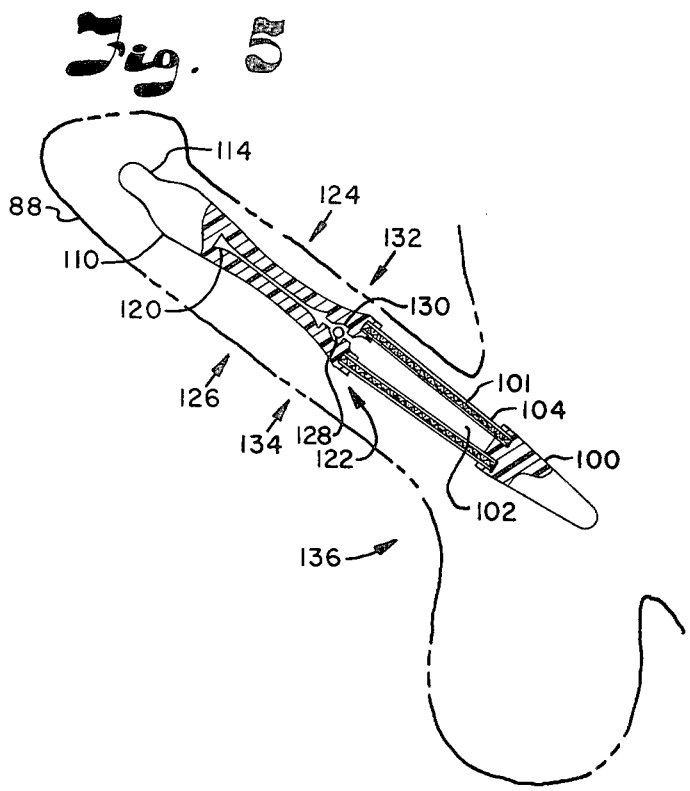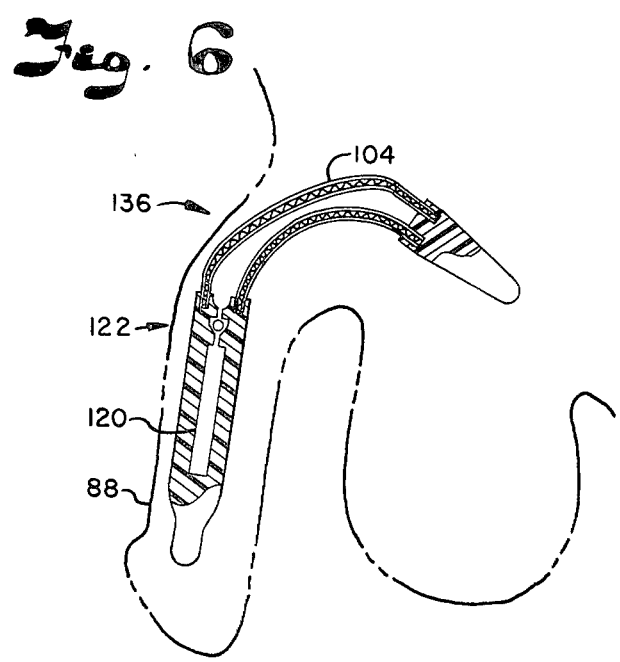

PENILE PROSTHESIS

BACKGROUND OF THE INVENTION

This is a continuation-in-part of U.S. application Ser. No. 28,979 entitled "Medical Prosthetic Pull Valve" filed Apr. 11, 1979, now U.S. Pat. No. 4,224,934 by applicants Frank Brantley Scott, Jr. and John H. Burton.

This invention relates generally to the field of implantable medical prosthetic devices for curing male erectile impotence and relates more particularly to penile prosthetic implants operated by fluid pressure supplied from a pump means.

The use of an implantable, inflatable prosthesis for the management of erectile impotence is described by Scott et al in *Urology*, Vol. II, No. 1, July 1973, pp. 80–82. The article describes an inflatable penile prosthesis constructed of Dacron reinforced silicone rubber and consisting of four main parts: a reservoir to hold a radiopaque fluid which was used to activate the device, two pumping mechanisms for inflating and deflating the fourth part, which was the penile prosthesis. The inflatable penile prosthesis included two cylindrical bodies which tapered at each end and which were placed inside the corpora bodies of the penis. An implantable fluid transfer system for the treatment of impotence is described by Kothari et al in the *Journal of Biomechanics*, Vol. 5, 1972, pp. 567–570. Kothari et al describe a penile prosthesis consisting of two fluid filled collapsible tubes constructed of Dacron reinforced silicone rubber and having a shape simulating the corpora cavernosa.

A method and device for achieving a penile erection is described by Strauch et al in U.S. Pat. No. 3,853,122. Strauch et al disclose an elongated, flexible and stretchable hollow tube implanted in the penis. A flexible container is provided which contains a fluid which may be displaced into the tube to render the tube relatively rigid, thus providing the desired erection. A penile erection system is disclosed by Buuck in U.S. Pat. No. 3,954,102. Buuck shows a pair of inflatable and collapsible cylinders that are able to perform the function of the corpora cavernosa. Each cylinder includes a cylindrical silicone rubber body or sleeve which is expansible circumferentially and also longitudinally.

Another penile prosthesis for the management of erectile impotence is described by Uson in U.S. Pat. No. 4,009,711. Uson shows a body member having a nondistensible portion and a distensible body portion, with the latter being connected by suitable conduit means to a fluid supply source. The nondistensible portion is preferably made of plastic material, such as Silastic, which is semirigid, and is adapted to be implanted into the root end of the corpus cavernosum of the penis. The Uson penile prosthesis basically comprises a semirigid nondistensible portion or a tail which is preferably formed unitary with an inflatable or distensible body portion, with the distensible body portion in communication with a fluid supply means. The distensible body portions have an elongated configuration and are inserted within the tunica of the corpora cavernosa all the way up to the glans penis. The prosthesis is rigid at the root of the penis and inflatable at the pendulous portion of the penis.

Timm and Burton disclose a malleable penile prosthesis which may be conformed to any desired shape in U.S. Pat. No. 3,987,789. The penile prosthesis comprises at least one elongated, malleable rod portion adapted to be selectively conformed to a desired shape; and a generally tubular, physiologically inert covering for incapsulating said rod portion. The prosthesis includes a portion positioned within the pubic symphysis of the patient and functioning to anchor the prosthesis in the desired position within the penis. A composite rod penile implant including a very flexible hinge portion is disclosed by Finney and Lynch in U.S. Pat. No. 4,066,073. The hinged portion is positioned at the base of the penis below the pelvic bone and permits the penis to be conveniently and easily bent. The implant itself comprises an elongated rod formed of silicone rubber or other suitable material positionable within the corpus cavernosum of the penis. Stiff proximal and distal portions of the implant provide desired stiffness to the penis while the hinge portion permits it to be conveniently and easily bent.

Prior art inflatable penile prostheses have required relatively large fluid reservoirs to contain the amount of fluid necessary to inflate elongated, stretchable hollow tubes implanted in the penis. It is disadvantageous to implant a large fluid reservoir in the scrotum. It is also disadvantageous to implant separate structures, including a fluid reservoir and fluid conduits, at a location remote from the penis or from a pump means implanted in the scrotum.

A drawback to prior art rod type penile prostheses is their inabilitity to provide a stiff erection and to provide an easily bendable condition. Another drawback to prior art rod type penile prostheses is their inability to expand longitudinally. A further drawback to prior art rod type penile prostheses is that precise adjustment of the length of each prosthesis is necessary to properly fit each individual patient. Such length adjustments are necessary to prevent undesirable pressure necrosis and to prevent erosion or extrusion of the prosthesis from the patient's penis.

BRIEF SUMMARY OF THE INVENTION

It is therefore an object of this invention to provide a penile prosthesis for implantation in a human male patient to cure erectile impotence. It is a further object of this invention to provide a penile prosthesis for which a user may select between a stiff, erect condition and a nonerect, easily bendable condition.

Another object of this invention is to provide a penile prosthesis presenting less of a risk of causing pressure necrosis or extrusion of the prosthesis than prior art rod type penile prostheses.

A further object of this invention is to provide a penile prosthesis which may be implanted, in part, in the scrotum but which does not occupy so much of the intrascrotal space so as to interfere with the functioning of bodily organs contained therein.

It is a further object of this invention to provide a penile prosthesis which does not require the surgical implantation of structures at bodily locations remote from the penis.

Another object of this invention is to provide a penile prosthesis which stretches longitudinally to effectively lengthen the penis when the penile prosthesis is placed in an erect condition from a nonerect, bent condition.

A further object of this invention is to provide a penile prosthesis requiring the transfer of only a small volume of fluid to cause the penile prosthesis to go between a nonerect and an erect condition.

Briefly, this penile prosthesis invention consists of a rigid front portion for mounting inside the distal portion of a penis, a rigid rear portion for mounting inside the proximal portion of the penis, and a tubular section attached to and mounted between the front portion and the rear portion so as to define a chamber which is connected to a pump means. The pump means is actuateable to supply fluid pressure to the chamber and thus to force the penis into an erect condition. When fluid pressure is not supplied to the chamber, the penis is allowed to assume a bent condition. A valve means is placed between the pump means and the chamber means to allow control of fluid pressure maintained in the chamber.

The tubular section is collapsible but resists stretching so that the volume of the chamber undergoes only a small change as the penis is caused to go between a nonerect, bent condition and an erect condition.

These and other objects and advantages of this invention will appear more fully from the following description made in conjunction with the accompanying drawings wherein like reference characters refer to the same or similar parts throughout the several views.

BRIEF DESCRIPTION OF THE DRAWINGS

FIG. 5 is a partially cut away side view showing a penile prosthesis having a pump means positioned inside the front portion of the prosthesis, wherein the prosthesis is shown as implanted in a human male patient and in an erect condition, and wherein portions of the human anatomy including the penis and scrotum are shown in phantom; and FIG. 6 is a partially cut away side view showing the penile prosthesis as in FIG. 5, but wherein the prosthesis is in a bent condition.

DESCRIPTION OF THE PREFERRED EMBODIMENT

Figure 1:
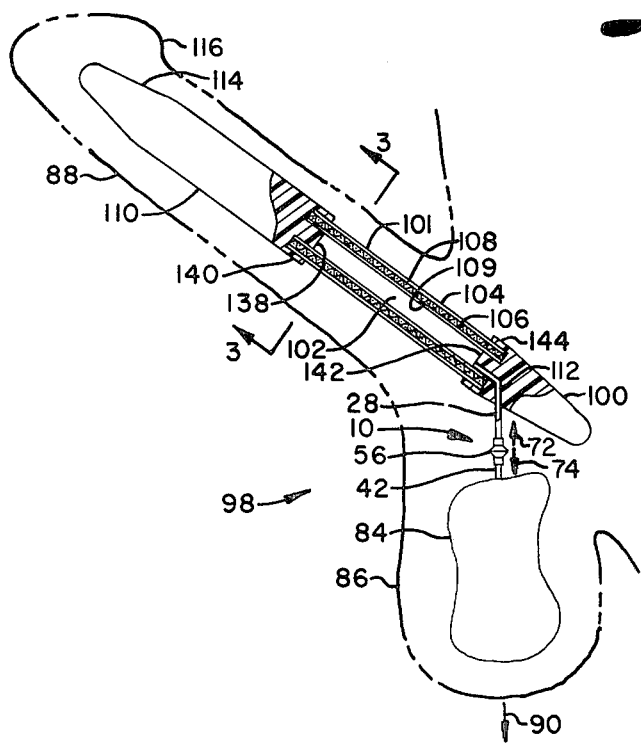
FIG. 1 is a partially cut away side view showing a penile prosthesis having a pump means positioned inside the scrotum, wherein the prosthesis is shown as implanted in a human male patient and in an erect condition, and wherein portions of the human anatomy including the penis and scrotum are shown in phantom.

Referring first to FIG. 1, penile prosthesis 98 is surgically implanted inside the penis 88 and scrotum 86 of a human male patient. Penile prosthesis 98 comprises a rigid front portion 110 mounted inside the distal portion of penis 88, a rigid rear portion 100 mounted inside the proximal portion of penis 88, and a hollow tubular section 101 attached to and mounted between the front portion 110 and the rear portion 100 so as to define an internal chamber means 102. Portions 100 and 110 and section 101 are mounted inside a corpus cavernosum of penis 88.

Front portion 110 is preferably solid and composed of a medical grade silicone elastomer which is substantially rigid so as to impart rigidity to penis 88 and thus provide for satisfactory erection of penis 88 when penis 88 and penile prosthesis 98 are placed in an erect condition. Front portion 110 is shaped as an elongated cylinder having a pointed, tapered tip 114 positioned under the glans 116 of penis 88 to reliably support the glans 116. Front portion 110 preferably comprises a solid elastomeric molding but may also comprise a hollow membrane filled with a viscous gel so as to form a structure which is substantially rigid yet not hard or unyielding. Front portion 110 is substantially rigid so as to perform its function of supporting the diameter of penis 88, to prevent bending of the pendulous portion of penis 88, and to provide support along the length of penis 88 when penis 88 is placed in an erect condition so that penis 88 maintains its length when exposed to thrusting forces during sexual intercourse.

Rigid rear portion 100 is positioned in the crus of penis 88 to reliably support tubular section 101 and front portion 110 so that a satisfactory erection of penis 88 results when penis 88 and penile prosthesis 98 are placed in an erect condition. When penile prosthesis 98 is placed in an erect condition, portions 100 and 110 and section 101 behave like a cantilevered beam wherein rear portion 100 behaves as if it is anchored to the patient's body to support the cantilevered beam. Rear portion 100 is preferably an elongated solid and composed of a medical grade silicone elastomer which is substantially rigid so as to reliably support the front portion 110 and tubular section 101 and thus provide for satisfactory erection of penis 88 when penis 88 and penile prosthesis 98 are placed in an erect condition.

Tubular section 101 is preferably an elongated, flexible, hollow right circular cylindrical tube. Tubular section 101 is long enough to allow penis 88 to bend freely when penile prosthesis 98 is placed in a nonerect condition. When penile prosthesis 98 is in a nonerect condition, the function of tubular section 101 is to allow penis 88 to bend freely so that penis 88 may be conveniently concealed in the patient's clothing. The positioning of tubular section 101 along the body-penis intersection allows bending or hinging of the penis to take place at that location. A further function of tubular section 101, when penile prosthesis 98 is in a nonerect condition, is to allow front portion 110 to fit loosely inside the length of a corpus cavernosum of penis 88 so that the pressure of front portion 110 bearing from the inside of penis 88 against the glans 116 is relieved so that pressure necrosis is prevented and so that front portion 110 does not erode or extrude from penis 88. When penile prosthesis 98 is in an erect condition, the function of tubular section 101 is to prevent bending of penis 88 and to support front portion 110 so that penis 88 remains rigid and maintains its length when exposed to thrusting forces during sexual intercourse.

Tubular section 101 comprises a tubular sheath 104 defining an internal chamber means 102 in the space bounded by portions 100 and 110 inside the sheath 104. Section 101 is slipped into and adhesively attached to front portion 110 and rear portion 100. Portions 100 and 110 have similar wide flaps having annual cross-sections and labeled 144 and 140, respectively. Section 101 is slipped into the space between the circular cylindrical plug 138 of front portion 110 and the flap 140 and is held in place by adhesives on the mating surfaces between section 101 and the plug 138 and flap 140. Similarly, section 101 is held in place between flap 144 and circular cylindrical plug 142 on rear portion 100. Alternatively, portions 100 and 110 could be molded onto section 101 as by dipping section 101 into suitably shaped containers (not shown) filled with a liquid silicone rubber molding compound so that portions 100 and 110 are molded to shape and become attached to section 101 during the molding process.

Sheath 104 is preferably formed using a three layer sandwich-type laminated construction having an inner tubular material 109 surrounded by a woven fabric mesh 106 which, in turn, is surrounded by an outer tubular material 108. Material 109 is preferably silicone rubber tubing which is impervious to the fluids contained in chamber means 102. Material 108 is preferably silicone rubber tubing which is impervious to body fluids. Fabric mesh 106 is preferably woven of DuPont Dacron Polyester brand fibers. Mesh 106 is a woven tube which substantially resists both radial and longitudinal stretching, but which will allow tubular sheath 104 and tubular section 101 to collapse and penile prosthesis 98 to assume a bent condition when fluid pressure is not supplied to chamber means 102. It is preferable to weave rather than knit the mesh 106, in order that radial and longitudinal stretching of tubular section 101 is prevented. It is desirable to prevent stretching of section 101 to minimize the change in volume of chamber means 102 as the pressure of fluid contained therein is changed.

Minimization of the change in internal volume of chamber means 102 as the pressure of fluid contained therein is changed allows pump means 84 to be made of a small size which occupies only so much of the intrascrotal space so as to not interfere with the functioning of bodily organs contained in the scrotum 86. Pump means 84 acts as a fluid reservoir for supplying fluid pressure to chamber means 102. Pump means 84 is preferably a thin, flexible, hollow bulb composed of an elastomeric, fluid impervious material. Pump means 84 resists stretching or ballooning so that when pump means 84 is actuated, sufficient fluid pressure results in chamber means 102 to cause penile prosthesis 98 to assume an erect condition. Pump means 84 is actuated to squeezing scrotum 86 thus compressing pump means 84 to supply fluid pressure to chamber means 102 and to transfer a volume of fluid to chamber means 102. Pump means 84 is in fluid communication with chamber means 102 by way of demand tubing 28, valve means 10, and supply tubing 42. Demand tubing 28 extends through rear portion 100 and is connected with chamber means 102 by way of fluid port 112.

A fluid such as biologically compatible, radiopaque contrast material is used to fill penile prosthesis 98 and does fill chamber means 102, demand tubing 28, valve 10, supply tubing 42, and pump means 84. When pump means 84 is actuated, fluid pressure is supplied to chamber means 102 and a volume of fluid (equal to the change in volume of chamber means 102 as the pressure of fluid contained therein is changed) is transferred from pump means 84 to chamber means 102. It is desirable to minimize the change in volume of chamber means 102 and thereby minimize the change in volume of pump means 84 when pump means 84 is actuated, so that the size of pump means 84 is small and so that the surgical implantation of structures such as fluid reservoirs at bodily locations remote from the penis 88 is not required. The fluid used to fill the penile prosthesis 98 is preferably isotonic (having the same salt concentration as the body fluids) and is preferably a relatively incompressible liquid so as to not substantially decrease in volume when penile prosthesis 98 is placed in an erect condition. Thus, the relative incompressability of said fluid allows the pump means 84 to be of small size.

Valve means 10 is a medical prosthetic pull valve as disclosed in application Ser. No. 28,979 entitled "Medical Prosthetic Pull Valve" which was filed Apr. 11, 1979, and which is incorporated herein by reference. Valve means 10 is in fluid communication with chamber means 102 by way of demand tubing 28. Also, valve means 10 is in fluid communication with pump means 84 by way of supply tubing 42. Valve means 10 includes an extensible section 56 having a contracted state and an extended state corresponding to a first state and a second state, respectively, for valve means 10. When section 56 is contracted, as in FIG. 1, valve means 10 is in its first state such that valve means 10 acts as a check valve allowing fluid flow only from pump means 84 to the chamber means 102. When valve means 10 is in its first state, fluid pressure is maintained in chamber means 102. Valve means 10 is normally in its first state and its first state corresponds to penile prosthesis 98 and penis 88 being free to assume a nonerect, bent condition or being maintained in an erect condition.

Valve means 10 may be operated by a user so as to select between the first state and the second state of valve means 10. Valve means 10 is operated to extend the extensible section 56 by applying opposing forces to valve means 10 in the direction of the arrows 72 and 74. Such opposing forces may be generated by applying a pulling force on pump means 84 within scrotum 86 in the direction of arrow 90. When extensible section 56 is extended so that valve means 10 is in its second state, fluid pressure is allowed to release from chamber means 102 and fluid is allowed to flow from chamber means 102 to pump means 84. The second state of valve means 10 is a transitory condition used to allow penile prosthesis 98 and penis 88 to go from an erect condition to a nonerect, bent condition.

Figure 2:
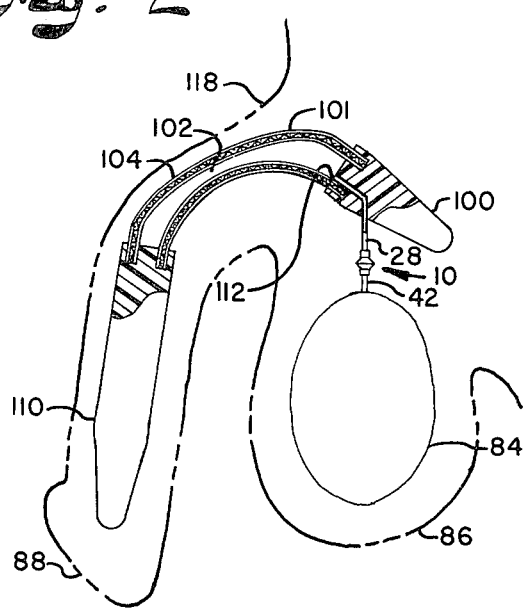
FIG. 2 is a partially cut away side view showing the penile prosthesis of FIG. 1, but wherein the prosthesis is in a bent condition.

Referring next to FIG. 2, penile prosthesis 98 and penis 88 are shown in a nonerect, bent condition. Chamber means 102 is not supplied with fluid pressure from pump means 84, and tubular sheath 104 is collapsed, thus allowing penis 88 to bend or swing pendulously upwards or downwards at its base 118. Front portion 110 imparts rigidity to the pendulous portion of penis 88 even though penis 88 is allowed to assume a nonerect, bent condition. When in such a nonerect condition, penis 88 may be bent at base 118 to allow its concealment in the clothing of the patient. It is preferable that tubular section 101 be positioned inside and along the length of penis 88 in a region near base 118 so that penis 88 is allowed to bend at its point of protrusion from the patient's body. When section 101 is so positioned, penis 88 is allowed to bend within the length of section 101.

In FIG. 1, pump means 84 is shown in a collapsed condition and tubular sheath 104 is not collapsed. In FIG. 2, pump means 84 is not collapsed and tubular sheath 104 is shown in a collapsed condition.

Figure 3:
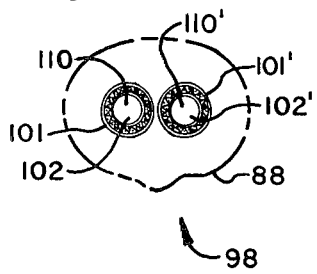
FIG. 3 is a cross sectional view of the penile prosthesis take along the lines and in the direction of the arrows 3—3 of FIG. 1, wherein the penis is shown in phantom.

Referring next to FIG. 3, a pair of front portions 110, 110' and tubular sections 101, 101' are positioned side by side inside the corpora cavernosa of penis 88. Although not shown here, a pair of rear portions like rear portion 100 are similarly positioned side by side inside the corpora cavernosa of penis 88 and demand tubing 88 is shaped like a "Y" in order to connect valve means 10 with each of a pair of chamber means 102, 102' located inside the pair of tubular sections 101, 101'. The pair of tubular sections 101, 101' cooperate and act in concert, when supplied with fluid pressure, to place penis 88 and penile prosthesis 98 in an erect condition. Front portion 110, tubular section 101, and rear portion 100 are duplicated identically to form a pair of identical assemblies extending along the two corpora cavernosa of penis 88. Alternatively, chamber means 102, 102' could be independently connected to a separate pump means like pump means 84, thus fluidically isolating chamber means 102 from chamber means 102' so that if one of the chamber means 102 and 102' should fail due to fluid leakage, the other would still function.

Figure 4:
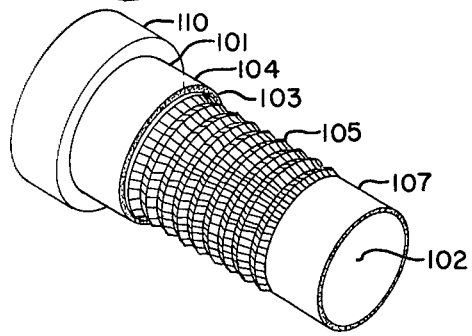
FIG. 4 is a partially cut away perspective view of a portion of one version of the penile prosthesis invention.

Referring next to FIG. 4, an alternative construction to that shown in FIGS. 1-3 is shown for tubular sheath 104. Here tubular sheath 104 comprises an outer layer 103, a corrugated layer 105, and an inner layer 107. Corrugated layer 105 is composed of cicumferentially corrugated tubular material having folds or pleats arranged about the circumference of layer 105 to form parallel and alternating ridges and grooves. Layer 105 behaves much like an accordion or a bellows in that it substantially resists radial stretching but is longitudinally stretchable. Layer 105 allows tubular section 101 to stretch longitudinally to effectively lengthen penis 88 when the penile prosthesis 98 is placed in an erect condition from a nonerect, bent condition. It is desirable to lengthen penis 88 when penis 88 is placed in an erect condition; however, the stretching of section 101 is necessarily limited so that the required size of pump means 84 is not unduly increased. Layers 103 and 107 are preferably composed of expandable silicone tubing which is impervious to fluids and are attached to the outside and inside, respectively, of layer 105. Layer 105 is preferably composed of vascular graft material woven of Dupont Dacron brand polyester fibers to resist radial stretching but circumferentially pleated into corrugations to permit longitudinal stretching.

As a further alternative, tubular sheath 104 could comprise a single collapsible tube (not shown) composed of a flexible material such as a urethane plastic which resists radial and longitudinal stretching.

Referring next to FIG. 5, penile prosthesis 136 is shown as an alternative construction to that shown in FIGS. 1 and 2. Here, pump means 120 performs the functions of pump means 84, and valve means 122 performs the functions of valve means 10. Pump means 120 is a hollow circular cylindrical chamber inside front portion 110. Pump means 120 is actuateable to supply fluid pressure to chamber means 102 by laterally squeezing the distal portion of penis 88 at the locations and in the directions indicated by arrows 124 and 126. When pump means 120 is actuated, front portion 110 collapses slightly, the volume inside pump means 120 decreases slightly, and fluid is transferred from pump means 120 to chamber means 102. The same type of fluid is used to fill penile prosthesis as was described above as filling prosthesis 98.

Valve means 122 comprises a ball 128 positioned inside a valve housing 130 and may be of the type disclosed as valve means 46 by Aurelio C. Uson in U.S. Pat. No. 4,009,711, which is incorporated herein by reference. Valve means 122 has a first state and a second state which serve the same functions as the respective states of valve means 10. Valve means 122 is normally in its first state and may be operated to place it in its second state by laterally squeezing the distal portion of penis 88 at the locations and in the directions indicated by arrows 132 and 134. Valve means 122, pump means 120, and chamber means 102 are in fluid communication and are filled with fluid.

Referring next to FIG. 6, penile prosthesis 136 and penis 88 are shown in a nonerect, bent condition. In FIG. 5, pump means 120 and front portion 110 are shown in a collapsed condition and tubular sheath 104 is not collapsed. In FIG. 6, pump means 120 and front portion 110 are not collapsed and tubular sheath 104 is shown in a collapsed condition. The prosthesis 136 of FIGS. 5 and 6 has a cross sectional shape identical to that shown in FIG. 3 and consists of a pair of side by side identical assemblies, with each assembly constructed as shown in FIGS. 5 and 6, with the pair of assemblies extending along the two corpora cavernosa of penis 88, and with the assemblies cooperating and acting in concert to allow a user to control the erection of penis 88.

OPERATION

The prosthesis 98 of FIGS. 1 and 2 is normally maintained in the nonerect condition of FIG. 2 which allows penis 88 to be concealed by the patient's clothing. When an erection of penis 88 is to be produced, pump means 84 is actuated by a user manually squeezing pump means 84 through scrotum 86. Valve means 10 allows fluid to flow from pump means 84 to chamber means 102 so that pressure is supplied to chamber means 102 and penis 88 assumes an erect condition. Valve means 10 maintains fluid pressure inside chamber means 102 so that penis 88 remains erect when pump means 84 is no longer actuated. Thus, valve means 10 maintains the erection of penis 88 during the act of sexual intercourse.

When penis 88 is to be placed in a nonerect, bent condition, the user applied a pulling force on pump means 84 within the scrotum 86 in the direction of arrow 90. Such a pulling force operates valve means 10 to allow the release of fluid pressure from chamber means 102 and to allow fluid flow from chamber means 102 to pump means 84. When fluid pressure is released from chamber means 102, tubular sheath 104 collapses and penis 88 is allowed to assume a nonerect, bent condition.

Operation of the penile prosthesis 136 of FIGS. 5 and 6 is quite similar to that of prosthesis 98 of FIGS. 1 and 2. Prosthesis 136 is normally maintained in the nonerect condition of FIG. 6. When an erection of penis 88 is to be produced, pump means 120 is actuated by a user manually squeezing the distal portion of penis 88 as indicated by arrows 124 and 126. Valve means 122 allows fluid to flow from pump means 120 to chamber means 102 so that penis 88 assumes an erect condition. Valve means 122 maintains the erection of penis 88 during the act of sexual intercourse.

When penis 88 is to be placed in a nonerect, bent condition, the user squeezes the distal portion of penis 88 as indicated by arrows 132 and 134. Such squeezing allows the release of fluid pressure from chamber means 102 and allows penis 88 to assume a nonerect, bent condition.

The minimal change in volume of chamber 102 which takes place between its collapsed and non-collapsed conditions, due to the construction of tubular sheath 104 as set forth herein, permits minimal fluid displacement between the pump means and chamber 102 to achieve an erection or to place the penis in a nonerect, bent condition. This is true of both embodiments of the penile prosthesis disclosed with respect to FIGS. 1, 2 and FIGS. 5, 6. This eliminates the need for a separate, remotely implanted fluid reservoir to hold a relatively large transfer volume of actuating fluid, as is required with previously known stretchable and fully distensible, inflatable penile prostheses.

It is anticipated that various changes may be made in the shape, construction and operation of the invention as disclosed herein without departing from the spirit and scope of the invention as defined by the following claims.

What is claimed is:

1. An implantable penile prosthesis comprising:
an elongated front portion for mounting inside the distal portion of a patient's penis, said front portion comprising a cylinder which is substantially rigid so as to impart rigidity to said penis and thus provide for satisfactory erection of said penis, when said penile prosthesis is implanted in said penis and when said penile prosthesis is placed in an erect condition.
a rear portion for mounting inside the proximal portion of said penis;
a tubular section attached to and mounted between said front portion and said rear portion, and having a collapsible tubular sheath and an internal chamber means so that said penile prosthesis assumes an erect condition when fluid pressure is supplied to said chamber means and so that said penile prosthesis is allowed to assume a nonerect, bent condition when fluid pressure is allowed to release from said chamber means wherein said tubular sheath is allowed to collapse when said penile prosthesis assumes a nonerect, bent condition so that when said penile prosthesis is implanted in said penis, said penis is allowed to bend in a region within the length of said tubular section; and
a pump means actuateable to supply fluid pressure to said chamber means.

2. An implantable penile prosthesis comprising:
an elongated, substantially rigid, generally cylindrical, front portion for mounting inside the distal portion of a patient's penis;
a rear portion for mounting inside the proximal portion of said penis;
a pump means; and
a tubular section attached to and mounted between said front portion and said rear portion, and having a tubular sheath defining an internal chamber means in fluid communication with said pump means, said tubular sheath being collapsible but nonstretchable, so that said penile prosthesis is actuateable between an erect and a nonerect condition by the transfer of a small volume of fluid between said pump means and said chamber means.

3. The penile prosthesis of claim 1 or claim 2 further comprising a valve means in fluid communication with said chamber means and having a first state and a second state, wherein fluid is maintained in said chamber means when said valve means is in said first state, wherein fluid is allowed to release from said chamber means when said valve means is in said second state, and wherein a user may operate said valve means so as to select between said first state and said second state.

4. The penile prosthesis of claim 1 or claim 2 wherein said pump means is positioned inside said front portion and wherein, when said penile prosthesis is implanted in said penis, said pump means is actuateable to supply fluid to said chamber means by laterally squeezing said distal portion of said penis.

5. The penile prosthesis of claim 1 or claim 2 wherein said section comprises a length of material which substantially resists radial stretching but which is longitudinally stretchable.

6. The penile prosthesis of claim 5 wherein said section comprises a length of circumferentially corrugated tubular material.

7. The penile prosthesis of claim 1 or claim 2 wherein said section substantially resists longitudinal and radial stretching.

8. The penile prosthesis of claim 6 wherein said section comprises a woven tubular mesh and wherein said tubular mesh substantially resists radial and longitudinal stretching.

9. The penile prosthesis of claim 1 or claim 2 wherein said tubular section, when said penile prosthesis is implanted in said penis, is beneath the base of said penis so that said penis is allowed to bend at its point of protrusion from the body of said patient.

10. The penile prosthesis of claim 1 or claim 2 wherein said front portion comprises a viscous gel filled cylinder to provide for satisfactory erection of said penis by imparting rigidity to said penis when said penile prosthesis is placed in an erect condition and when said penile prosthesis is implanted in said penis.

11. The penile prosthesis of claim 1 or claim 2, and further comprising a medical prosthetic pull valve in fluid communication with said chamber means and having an extensible section such that said pull valve acts as a check valve to maintain fluid in said penile prosthesis when said extensible section is not extended, and such that said pull valve acts to allow fluid to drain from said chamber means when said extensible section is extended, and wherein said extensible section extends when pulling forces are exerted along the length of said pull valve.

12. The penile prosthesis of claim 11 wherein said pull valve is connected between said tubular section and said pump means, and wherein said pump means is to be implanted in a patient's scrotum, so that said extensible section extends when downward pulling forces are exerted on said pump means through said scrotum.

13. The penile prosthesis of claim 1 or 2 wherein said front portion comprises a substantially solid cylinder.

14. The penile prosthesis of claim 4 wherein said pump means comprises a hollow, cylindrical chamber inside said elongated front portion, the walls of said front portion being displaceable inwardly towards each other in response to the lateral squeezing of said distal portion of said penis to reduce the volume of said cylindrical chamber and thereby force fluid into said chamber means.

* * * * *